United States Patent [19]

Leir

[11] Patent Number: 4,642,384

[45] Date of Patent: Feb. 10, 1987

[54] PROCESS FOR THE PREPARATION OF DERIVATIVES OF PYRROLIDINE AND PIPERIDINE

[75] Inventor: Charles M. Leir, New Richmond, Wis.

[73] Assignee: Riker Laboratories, Inc., St. Paul, Minn.

[21] Appl. No.: 772,470

[22] Filed: Sep. 4, 1985

Related U.S. Application Data

[63] Continuation of Ser. No. 269,070, Jun. 2, 1981, abandoned, which is a continuation of Ser. No. 158,992, Jun. 12, 1980, abandoned, which is a continuation of Ser. No. 21,331, Mar. 19, 1979, abandoned.

[51] Int. Cl.$^4$ .............................................. C07C 49/80
[52] U.S. Cl. .................................... 568/337; 546/224
[58] Field of Search ................ 568/337; 564/183, 184, 564/185, 139, 133, 142

[56] References Cited

U.S. PATENT DOCUMENTS

| | | | |
|---|---|---|---|
| 2,964,557 | 12/1960 | Pribyl et al. | 568/337 |
| 3,655,728 | 4/1972 | Mendel | 560/85 |
| 3,748,361 | 7/1973 | Rosenfeld et al. | 568/337 |
| 3,869,513 | 3/1975 | Buckman et al. | 568/337 |
| 3,900,481 | 8/1975 | Banitt et al. | 260/293.77 |
| 3,967,949 | 7/1976 | Benefiel et al. | 568/337 |
| 4,071,524 | 1/1978 | Banitt | 260/293.77 |
| 4,123,533 | 10/1978 | Hermecy et al. | 514/258 |

OTHER PUBLICATIONS

Atherton, et al., J. Chem. Soc., pp. 660–663, (1945).
Chemical Abstracts 59, 12678h, (1963).
Netherlands Laid-Open Application 7407245, face page and pp. 8, 9 and 10.
Chemical Abstracts 46:7068g.
Chemical Abstracts 50:11971c.
Chemical Abstracts 62:10310d.

*Primary Examiner*—James H. Reamer
*Attorney, Agent, or Firm*—Donald M. Sell; James A. Smith; Robert W. Sprague

[57] ABSTRACT

Processes and intermediates for the preparation of the antiarrhythmic agent 2,5-bis(2,2,2-trifluoroethoxy)-N-(2-piperidylmethyl)benzamide.

3 Claims, No Drawings

PROCESS FOR THE PREPARATION OF DERIVATIVES OF PYRROLIDINE AND PIPERIDINE

This is a continuation of application Ser. No. 269,070 filed June 2, 1981, now abandoned, which is a continuation of application U.S. Ser. No. 158,992 filed June 12, 1980, now abandoned, which is a continuation of application U.S. Ser. No. 21,331 filed Mar. 19, 1979, now abandoned.

TECHNICAL FIELD

This invention relates to processes and intermediates for preparing certain antiarrhythmic agents.

SUMMARY OF THE INVENTION

In one aspect of the invention, a method of preparing a 2,5-bis(2,2,2-trifluoroethoxy)-N-(2-piperidylmethyl)-benzamide is provided which comprises the following steps. Hydroquinone is contacted with 2,2,2-trifluoroethyl trifluoromethanesulfonate under conditions to yield 1,4-bis(2,2,2,-trifluoroethoxy)benzene. In the presence of a Lewis acid catalyst, the 1,4-bis(2,2,2-trifluoroethoxy)benzene is then treated with an acetylation agent under conditions to create 2,5-bis(2,2,2-trifluoroethoxy)acetophenone. Two of the three hydrogens on the acetophenone function of the 2,5-bis(2,2,2-trifluoroethoxy)acetophenone are thereafter substituted to yield first the alpha, alpha-dichloro-substituted 2,5-bis(2,2,2-trifluoroethoxy)acetophenone. Subsequently, in the presence of a buffering base, the third hydrogen of the alpha,alpha-dichloro-substituted 2,5-bis(2,2,2-trifluoroethoxy)acetophenone is substituted to yield alpha,alpha,alpha-trichloro-substituted 2,5-bis(2,2,2-trifluoroethoxy)acetophenone. The resultant alpha,alpha,alpha-trichloro-substituted 2,5-bis(2,2,2-trifluoroethoxy)acetophenone is then contacted with 2-aminomethylpyridine, whereby there is formed 2,5-bis(2,2,2-trifluoroethoxy)-N-(2-pyridylmethyl)benzamide. Finally, the 2,5-bis(2,2,2-trifluoroethoxy)-N-(2-pyridylmethyl)-benzamide is treated with an agent capable of hydrogenation of the aromatic bond in the heterocyclic ring, whereby there is formed a 2,5-bis(2,2,2-trifluoroethoxy)-N-(2-piperidylmethyl)benzamide. In a preferred method according to the foregoing, the 2,5-bis(2,2,2-trifluoroethoxy)-N-(2-piperidylmethyl)benzamide is recovered in the form of its acetate salt.

In another aspect of the invention, a method of preparing a 2,5-bis(2,2,2-trifluoroethoxy)-N-(2-piperidylmethyl)benzamide is provided which comprises the following steps. The compound 1,4-dibromobenzene is contacted with alkali metal 2,2,2-trifluoroethoxide in the presence of cuprous or cupric ion and in a strongly polar solvent comprising 2,2,2-trifluoroethanol to provide 1,4-bis(2,2,2-trifluoroethoxy)benzene. Then, in the presence of a Lewis acid catalyst, the 1,4-bis(2,2,2-trifluoroethoxy)benzene is treated with an acetylation agent under conditions to create 2,5-bis(2,2,2-trifluoroethoxy)acetophenone. Two of the three hydrogens on the acetophenone function of 2,5-bis(2,2,2-trifluoroethoxy)acetophenone are thereafter substituted to yield first the alpha,alpha-dichloro-substituted 2,5-bis(2,2,2-trifluoroethoxy)acetophenone. Subsequently, in the presence of a buffering base, the third hydrogen of the alpha,alpha-dichloro-substituted 2,5-bis(2,2,2-trifluoroethoxy)acetophenone is substituted to yield alpha,alpha,alpha-trichloro-substituted 2,5-bis(2,2,2-trifluoroethoxy)acetophenone. The resultant alpha,alpha,alpha-trichloro-substituted 2,5-bis(2,2,2-trifluoroethoxy)acetophenone is then contacted with 2-aminomethylpyridine, whereby there is formed 2,5-bis(2,2,2-trifluoroethoxy)-N-(2-pyridylmethyl)benzamide. Finally, the 2,5-bis(2,2,2-trifluoroethoxy)-N-(2-pyridylmethyl)-benzamide is treated with an agent capable of hydrogenation of the aromatic bond in the heterocyclic ring, whereby there is formed a 2,5-bis(2,2,2-trifluoroethoxy)-N-(2-piperidylmethyl)benzamide. In a preferred method according to the foregoing, the 2,5-bis(2,2,2-trifluoroethoxy)-N-(2-piperidylmethyl)benzamide is recovered in the form of its acetate salt.

In still another aspect of the invention, a method of preparing a 2,5-bis(2,2,2-trifluoroethoxy)-N-(2-piperidylmethyl)benzamide is provided which comprises the following steps. Hydroquinone is contacted with 2,2,2-trifluoroethyl trifluoromethanesulfonate under conditions to yield 1,4-bis(2,2,2-trifluoroethoxy)-benzene. In the presence of a Lewis acid catalyst, the 1,4bis(2,2,2-trifluoroethoxy)benzene is then treated with an acetylation agent under conditions to create 2,5-bis(2,2,2-trifluoroethoxy)acetophenone. Two of the three hydrogens on the acetophenone function of said 2,5-bis(2,2,2-trifluoroethoxy)acetophenone are thereafter substituted to yield first the alpha,alpha-dichloro-substituted 2,5-bis(2,2,2-trifluoroethoxy)acetophenone. Subsequently, in the presence of a buffering base, the third hydrogen of the alpha,alpha-dichloro-substituted 2,5-bis(2,2,2-trifluoroethoxy)acetophenone is substituted to yield alpha,alpha,alpha-trichloro-substituted 2,5-bis(2,2,2-trifluoroethoxy)acetophenone. Finally, the resultant alpha,alpha,alpha-trichloro-substituted 2,5-bis(2,2,2-trifluoroethoxy)acetophenone is contacted with 2-aminomethylpiperidine, whereby there is formed 2,5-bis(2,2,2-trifluoroethoxy)-N-(2-piperidylmethyl)-benzamide. In a preferred method according to the foregoing, the 2,5-bis(2,2,2-trifluoroethoxy)-N-(2-piperidylmethyl)benzamide is recovered in the form of its acetate salt.

In yet another aspect of the invention, a method of preparing a 2,5-bis(2,2,2-trifluoroethoxy)-N-(2-piperidylmethyl)benzamide is provided which comprises the following steps. The compound 1,4-dibromobenzene is contacted with an alkali metal 2,2,2-trifluoroethoxide in the presence of cuprous or cupric ion and in a strongly polar solvent comprising 2,2,2-trifluoroethanol to yield 1,4-bis(2,2,2-trifluoroethoxy)benzene. Then, in the presence of a Lewis acid catalyst, the 1,4-bis(2,2,2-trifluoroethoxy)benzene is treated with an acetylation agent under conditions to create 2,5bis(2,2,2-trifluoroethoxy)acetophenone. Two of the three hydrogens on the acetophenone function of the 2,5-bis(2,2,2-trifluoroethoxy)acetophenone are then substituted to yield first the alpha,alpha-dichloro-substituted 2,5-bis(2,2,2-trifluoroethoxy)acetophenone. Subsequently, in the presence of a buffering base, the third hydrogen of the alpha,alpha-dichloro-substituted 2,5-bis(2,2,2-trifluoroethoxy)acetophenone is substituted to yield alpha,alpha,alpha-trichloro-substituted 2,5-bis(2,2,2-trifluoroethoxy)acetophenone. Finally, the resultant alpha,alpha,alpha-trichloro-substituted 2,5-bis(2,2,2-trifluoroethoxy)acetophenone is contacted with 2-aminomethylpiperidine, whereby there is formed 2,5-bis(2,2,2-trifluoroethoxy)-N-(2-piperidylmethyl)-benzamide. In a preferred method according to the foregoing, the 2,5-bis(2,2,2-trifluoroethoxy)-N-(2- piperidylmethyl)benzamide is recovered in the form of its acetate salt.

In still another aspect of the invention, there is provided the compound 2,5-bis(2,2,2-trifluoroethoxy)acetophenone which is a useful intermediate in the processes of the invention.

In yet another aspect of the invention, there is provided the compound 2,5-bis(2,2,2-trifluoroethoxy)alpha,alpha-dichloroacetophenone which is also a useful intermediate in the processes of the invention.

In still another aspect of the invention, there is provided the compound 2,5-bis(2,2,2-trifluoroethoxy)alpha,alpha,alpha-trichloroacetophenone which is also a useful intermediate in the processes of the invention.

The compound 2,5-bis(2,2,2-trifluoroethoxy)-N-(2-piperidylmethyl)benzamide, an antiarrhythmic agent, is disclosed in U.S. Pat. No. 3,900,481.

DETAILED DESCRIPTION

Specifically, the present invention relates to a process for preparing a compound of the formula

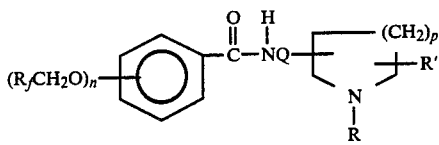

wherein $R_f$ is a perfluoroalkyl radical containing one to three carbon atoms, n is one of three, p is one of two, Q is a carbon to nitrogen bond, methylene or methylmethylene and R and R' are individually hydrogen, methyl or ethyl which comprises (1) reacting a compound of the formula

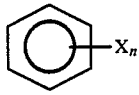

wherein all of the X's are the same and are selected from OH and Br with a suitable alkylating agent of the formula

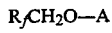

wherein A is —SO$_2$CF$_3$ or an alkali metal to provide a compound of the formula

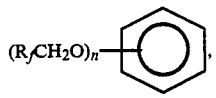

(2) acetylating in the presence of a Lewis acid catalyst to provide a substituted acetophenone of the formula

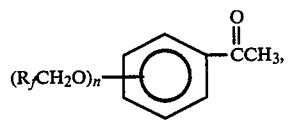

(3) chlorinating the substituted acetophenone to form the corresponding α,α-dichloroacetophenone

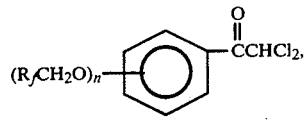

(4) adding a buffering base and further chlorinating to provide the α,α,α-trifluoroacetophenone

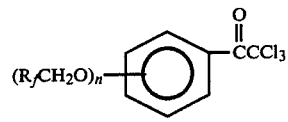

and (5) reacting that product alternatively with a compound of the formula

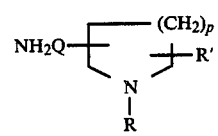

to form the desired product in one step or with a compound of the formula

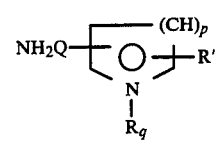

in which q is one when p is one and q is zero when p is two, then reducing to form the desired product.

Preferably, the process is utilized to prepare antiarrhythmic agents in which $R_f$ is CF$_3$, most preferably of the formula

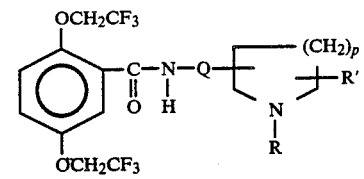

due to the superior properties of such compounds as antiarrhythmics.

The processes which comprises steps (1); (1)–(2); (3); (4); (3)–(4); and (5) above constitute separate aspects of the overall invention as do the intermediate compounds

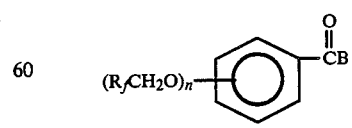

wherein $R_f$ is a perfluoroalkyl radical containing one to three carbon atoms, n is one to three and B is selected from —CH$_3$, —CHCl$_2$ and CCl$_3$.

The overall process of the invention follows the reaction sequence:

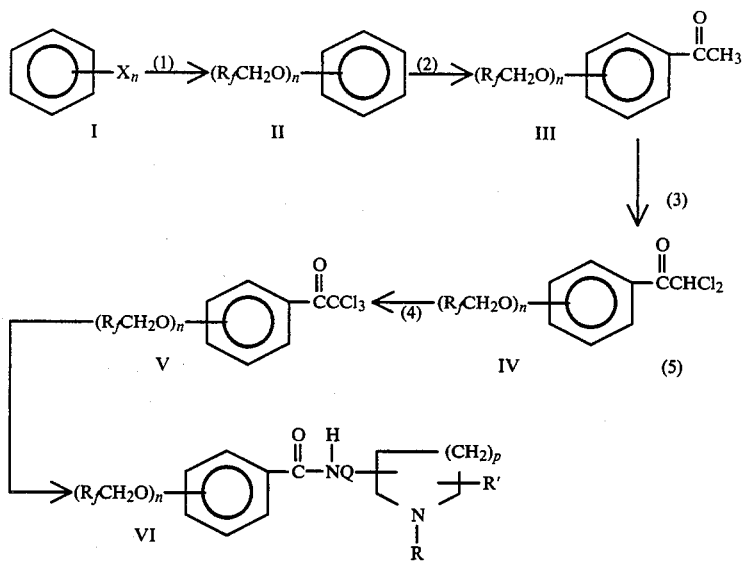

in which the compounds VI are the antiarrhythmic agents previously alluded to.

Preferably, in the foregoing reaction sequence, Q is (1) a carbon-nitrogen bond and is bonded to the 3 position of the pyrrolidine or piperidine ring or (2) a methylene linking group bonded to the 2 position of the piperidine or pyrrolidine ring. Most preferred is the process for preparing the compound of formula VI wherein O is methylene bonded to the 2 position of a piperidine ring (i.e. in which p is 2) and R and R' are both hydrogen.

In the first step of the process, when X is OH, A is suitably —SO₂CF₃ and the reactants are heated together in a solvent such as acetone or N,N-dimethylformamide and in the presence of a base, preferably a weak base such as an alkali metal carbonate, e.g. potassium or sodium carbonate.

When X is Br, the bromobenzene I is reacted with the 1,1-dihydroperfluoroalkoxide ion in a strongly polar solvent mixture at a temperature up to the reflux temperature of the solution in the presence of cuprous or cupric ion to provide the desired product II in good yield. The 1,1-dihydroperfluoroalkoxide ion is obtained from the corresponding alcohol by reaction with a strong base such as sodium hydroxide or preferably sodium hydride. Suitable solvent mixtures include dimethyl sulfoxide, N,N-dimethylacetamide and preferably N,N-dimethylformamide, each with about 10 to 15 percent, and preferably about 20 percent, of the 1,1-dihydroperfluoroalcohol (which corresponds to the 1,1-dihydroxyperfluoroalkoxide ion). Cuprous ion is provided, e.g. by a cuprous halide such as cuprous iodide or cuprous bromide. Cupric ion is provided e.g. by cupric bromide, cupric sulfate or cupric acetate.

In step (2) the 1,1-dihydroperfluoroalkoxy-substituted benzene II produced in the first step is acetylated by reacting under mild conditions with any acetylating agent such as acetyl chloride or acetic anhydride in the presence of a Lewis acid catalyst such as tin chloride, ferric chloride or, preferably, aluminum chloride. The acetylation is carried out in a suitable non-reactive solvent such as a chlorinated hydrocarbon, such as dichloromethane, trichloroethylene or 1,2-dichloroethane, diethyl ether, tetrahydrofuran and the like. Unexpectedly, this reaction provides high yields of the desired substituted acetophenone III.

The reaction of step (3) is a simple chlorination of the intermediate III in a suitable solvent such as ethyl acetate, a chlorinated hydrocarbon or, preferably, in acetic acid solution. This reaction is carried out at a moderate temperature, preferably 50° to 60° C.

The product IV can be isolated if desired, or the chlorination carried on as in step (4) to obtain the intermediate V by adding a buffering agent e.g. an acetate salt such as sodium acetate and raising the temperature slightly for example, to 80° to 100° C., while continuing the chlorination.

The final step of the process may be carried out directly from a saturated diamine

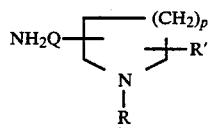

or indirectly from an unreduced diamine

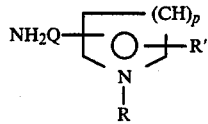

Thus, a saturated ring-containing compound such as a 2-aminomethylpiperidine, 2-aminomethylpyrrolidine, 3-aminopiperidine or 3-aminopyrrolidine can be reacted with the trichloroacetophenone product of step (4) or, a compound such as a 2-aminomethylpyridine, 2-aminomethylpyrrole, 3-aminopyridine or 3-aminopyrrole can be reacted with the trichloroacetophenone product of step (4). In either case, the reaction proceeds readily without external heating in an inert solvent such as toluene, benzene, isopropyl alcohol, cyclohexane and the like. The reaction proceeds particularly readily and in high yield when the unreduced diamine is reacted in a mixture of toluene and cyclohexane. The resulting adduct is reduced to the desired product VI by catalytic hydrogenation in the presence of platinum oxide or (preferably) platinum on carbon. The solvent used for this reaction is methanol or a lower alkanoic acid such as (and preferably) glacial acetic acid and the preferred temperature range is 15° to 30° C.

The following examples illustrate the processes of the invention and the preparation of the intermediate products thereof, and are not intended to be limiting on the scope of the invention as described hereinabove.

EXAMPLE 1

Step (1) of the process: $A=SO_2CF_3$ and $X=OH$

To a mixture of 2.42 moles (334.4 g.) of potassium carbonate, 2.2 moles (510.6 g.) of 2,2,2-trifluoroethyl trifluoromethanesulfonate in 1.02 liters of acetone is added a solution of 1.0 mole (110 g.) of hydroquinone in 1.1 liters of acetone, slowly over a 2 hour period. The reaction is then heated at reflux for 24 hours, the reaction mixture is evaporated, and 2 liters of chloroform and 2 liters of water are added to the residue. The chloroform layer is separated, the aqueous layer is washed twice with 1 liter of chloroform, and the combined chloroform solution is washed with 1 liter of water. The chloroform solution is dried over magnesium sulfate, then concentrated under vacuum. Hexane is added to the residue and the solid product is collected by filtration and washed with hexane. Additional material is collected from the concentrated residues. A yield of 88 percent, 241 g. of 1,4-bis(2,2,2-trifluoroethoxy)benzene, m.p. 75°–77° C. is obtained.

EXAMPLE 2

Step (1) $A=Na$ and $X=Br$

To 0.20 mole (9.6 g.) of 50 percent sodium hydride in 40 ml. of N,N-dimethylformamide is added 40 ml. of 2,2,2-trifluoroethanol followed by 0.034 mole (8.0 g.) of 1,4-dibromobenzene and 0.006 mole (1.0 g.) of cuprous iodide. The mixture is heated at its reflux temperature for 4 hours, then cooled to about 25° C. and filtered. The residue is washed with N,N-dimethylformamide. The solution is then poured into water, and the precipitate is separated by filtration. The product is dissolved in diethyl ether and filtered, and the filtrate solution is evaporated to provide a solid residue which is washed with hexane and dried. The product is 7.3 g. (80 percent) of 1,4-bis(2,2,2-trifluoroethoxy)benzene, m.p. 77° to 79° C.

The reaction is rerun as follows, varying the conditions and proportions of the constituents and utilizing cupric bromide as the catalyst: To a mixture of 4.8 g. of sodium hydride in 40 ml. of N,N-dimethylformamide is added 20 ml. (27.4 g.) of 2,2,2-trifluoroethanol. To this mixture is added 0.034 mole (8.0 g.) of 1,4-dibromobenzene and 1.0 g. of cupric bromide. The reaction mixture is heated at about 100° C. for two hours, then quenched with ice water. Acidification with hydrochloric acid and filtration produces 9.2 g. (99 percent) of white solid 1,4-bis(2,2,2-trifluoroethoxy)benzene. The structure is confirmed by infrared spectral analysis.

EXAMPLE 3

Step (2) utilizing acetic anhydride as the acetylating agent

To a mixture of 2.43 moles (324 g.) of aluminum chloride in 648 ml. of dichloromethane is added a solution of 0.88 mole (274 g.) of 1,4-bis(2,2,2-trifluoroethoxy)benzene and 0.97 mole (92 ml.) of acetic anhydride in 880 ml. of dichloromethane over a 3 hour period while maintaining the temperature at above 0° C. The reaction mixture is then heated to its reflux temperature and stirred at reflux for 5 hours. The progress of the reaction is followed using thin-layer chromatography. The reaction mixture is placed in an ice bath and ice and 10 percent hydrochloric acid are added slowly to decompose the aluminum chloride complex. The temperature of the reaction mixture is not allowed to exceed 25° C. The organic phase is separated and washed once with 2 liters of 10 percent hydrochloric acid and then with 2 liters of water. The combined aqueous phase is extracted with several liters of dichloromethane. The organic phase is dried over magnesium sulfate, then evaporated to provide a moist residue. Hexane is added to the residue and the resulting solid is collected by filtration and washed with hexane. Upon drying, 250 g. of light yellow crystalline 2,5-bis(2,2,2-trifluoroethoxy)acetophenone is obtained. The yield is 90 percent, the m.p. is 84° to 86° C.

EXAMPLE 4

A scale up of the run of Example 3

To a mixture of 4,367 kilograms (32.75 moles) of aluminum chloride and 8.8 liters of dichloromethane at 0° C. is added gradually a solution of 3,267 kilograms of 1,4-bis(2,2,2-trifluoroethoxy)benzene and 1.399 kilograms (13.7 moles) of acetic anhydride in 1.3 liters of dichloromethane. The reaction temperature is maintained at 5° to 10° C. while stirring the mixture for about 16 hours. The reaction mixture is then heated to its reflux temperature and maintained under reflux for 4 hours. The reaction mixture is then acidified with 8.76 kilograms of 10 percent hydrochloric acid. Ice is added to the mixture to maintain the temperature below 20° C. The organic layer is separated and the aqueous layers are extracted several times with dichloromethane. The organic layers are dried, then evaporated to provide a residue which is triturated with hexane to provide a yellow solid product. Two crops of product are obtained providing a total yield of 3.088 kilograms of 2,5-bis(2,2,2-trifluoroethoxy)acetophenone, m.p. 84° to 88° C., yield 82 percent.

EXAMPLE 5

Step (2) utilizing acetyl chloride as the acetylating agent

To a mixture of 0.022 mole (2.8 g.) of aluminum chloride and 100 ml. of 1,2-dichloroethane is added dropwise at 25° C. a solution of 0.020 mole (5.6 g.) of 2,5-bis(2,2,2-trifluoroethoxy)benzene and 0.022 mole (1.7 g.) of acetyl chloride in 20 ml. of 1,2-dichloroethane. After stirring for 4 hours the reaction mixture is washed with ice water and hydrochloric acid and the organic layer is dried. Evaporation produces a residue which is recrystallized from hexane to provide 4.1 g. (71 percent) of pale yellow needles of 2,5-bis(2,2,2-trifluoroethoxy)acetophenone (as verified by infrared spectral analysis).

EXAMPLE 6

Step (3)

A mixture of 0.25 mole (79.1 g.) of 2,5-bis(2,2,2-trifluoroethoxy)acetophenone in 150 ml. of acetic acid is heated to 50° C. Chlorine gas is bubbled into the solution and the temperature increases gradually to 55° C. The chlorine addition rate is adjusted to maintain the temperature between 55° and 60° C. After about 75 minutes the temperature begins to decrease (indicating that no more chlorination is taking place). The total amount of chlorine added is 35.5 g. The resulting product is 2,5-bis(2,2,2-trifluoroethoxy)-α,α-dichloroacetophenone.

EXAMPLE 7

Step (4)

To the product of the preceding example (without isolation or purification) is added 0.35 mole (28.7 g.) of sodium acetate. The temperature increases to about 80° C., and the solution is heated to 85° C. Chlorine addition is resumed and the temperature increases to 100° C. After about 20 minutes the theoretical amount of chlorine has been taken up, and the mixture is poured into a mixture of ice and water. The precipitate which forms is collected by filtration, rinsed with water, dissolved in dichloromethane and dried. Evaporation provides a residue which is triturated with hexane to provide a white solid. A yield of 94 g. (90 percent) of 2,5-bis(2,2,2-trifluoroethoxy)-α,α,α-trichloroacetophenone, m.p. 45° to 48° C. is obtained.

EXAMPLE 8

Step (5) carried out in two reactions

To a solution of 0.05 mole (21.0 g.) of 2,5-bis(2,2,2-trifluoroethyl)-α,α,α-trichloroacetophenone in 60 ml. of toluene is added dropwise a solution of 0.055 mole (6.0 g.) of 2-aminomethylpyridine in 50 ml. of cyclohexane and 10 ml. of toluene. The reaction is exothermic, and a precipitate forms immediately. Additional toluene and cyclohexane are added to obtain a mixture consistency that permits stirring, and the stirring is continued for two hours at about 25° C. The solid is then separated by filtration, washed with a mixture of toluene and cyclohexane and dried to provide a white solid. The product is 2,5-bis(2,2,2-trifluoroethoxy)-N-(2-pyridylmethyl)-benzamide, m.p. 104°-106° C., 17.8 g., 89 percent yield.

A mixture of 0.33 mole (134.7 g.) of 2,5-bis(2,2,2-trifluoroethoxy)-N-(2-pyridylmethyl)benzamide, 1.347 liters of glacial acetic acid and 13.5 g. of 5 percent platinum on carbon is reduced in a Parr apparatus at about 30 pounds of hydrogen at room temperature. The reaction is complete in 6-7 hours. The reaction mixture is filtered and the catalyst is washed with isopropyl alcohol. The solution and washings are evaporated to provide a residue. Hexane is added to the residue and the resulting white solid is collected and recrystallized from a mixture of acetone and hexane. A 71 percent yield of 2,5-bis(2,2,2-trifluoroethoxy)-N-(2-piperidylmethyl)-benzamide acetate, m.p. 150° to 152° C., is obtained. By concentrating the residual liquid, an additional 18 percent of product is obtained as a second crop with a melting point of 148°-150° C.

EXAMPLE 9

Step (5) carried out in a single reaction

To a solution of 0.01 mole (4.19 g.) of 2,5-bis(2,2,2-trifluoroethoxy)-α,α,α-trichloroacetophenone in 50 ml. of isopropyl alcohol is added 0.01 mole (1.2 g.) of 2-aminomethylpiperidine. The mixture gradually turns solid over a period of 30 minutes. The mixture is allowed to sit for about 16 hours, then 0.01M of acetic acid and 5 ml. of isopropyl alcohol are added, and the solution is warmed to dissolve all of the solid. On cooling, 3.0 g. of a white solid are obtained. The filtrate is evaporated, and the residue recrystallized from isopropyl alcohol to give additional product as a white solid. The product is 2,5-bis(2,2,2-trifluoroethoxy)-N-(2-piperidylmethyl)benzamide acetate according to its infrared and nuclear magnetic resonance spectra.

What is claimed is:
1. 2,5-Bis(2,2,2-trifluoroethoxy)acetophenone.
2. 2,5-Bis(2,2,2-trifluoroethoxy)alpha,alpha-dichloroacetophenone.
3. 2,5-Bis(2,2,2-trifluoroethoxy)-alpha,alpha,alpha-trichloroacetophenone.

* * * * *